United States Patent

Hsieh

[11] Patent Number: 6,060,991
[45] Date of Patent: May 9, 2000

[54] DETECTING METHOD AND APPARATUS USING A PROGRAMMABLE MEMORY DEVICE FOR STORING A DIGITIZED REFERENCE VALUE

[75] Inventor: Shih-Hsiung Hsieh, Taipei Hsien, Taiwan

[73] Assignee: Everyday Technology Co., Ltd., Pan-Chiao, Taiwan

[21] Appl. No.: 09/086,765

[22] Filed: May 28, 1998

[30] Foreign Application Priority Data

Jan. 2, 1998 [TW] Taiwan ................................. 87200043

[51] Int. Cl.[7] .................................................. G08B 17/10
[52] U.S. Cl. ........................ 340/632; 340/577; 340/584; 340/628; 73/23.31; 73/31.01
[58] Field of Search ..................................... 340/577–579, 340/584, 628–630, 632–634; 73/23.31, 31.01

[56] References Cited

U.S. PATENT DOCUMENTS

| | | | |
|---|---|---|---|
| 4,420,746 | 12/1983 | Malinowski | 340/630 |
| 5,473,314 | 12/1995 | Mochizuki et al. | 340/630 |
| 5,526,280 | 6/1996 | Consadori et al. | 340/632 |
| 5,530,433 | 6/1996 | Morita | 340/628 |
| 5,543,777 | 8/1996 | Vane et al. | 340/630 |

*Primary Examiner*—Daniel J. Wu
*Attorney, Agent, or Firm*—Marger Johnson & McCollom, PC

[57] ABSTRACT

A detecting apparatus includes a processing device connected to a sensor, a programmable memory device and an alarm device. The sensor generates a signal output that varies according to a detected condition. The processing device includes a converting unit for converting the signal output of the sensor into a digitized value, a memory programming unit for storing a reference value in the memory device, and a comparing unit for comparing the digitized value from the converting unit with the reference value in the memory device. When the processing device is operated in a calibrating mode while the sensor is placed in a standard environment, the programming unit stores the digitized value from the converting unit as the reference value in the memory device. When the processing device is operated in the detecting mode while the sensor is installed in an environment to be detected, the processing device activates the alarm device upon detection by the comparing unit that the digitized value from the converting unit has exceeded the reference value in the memory device.

8 Claims, 4 Drawing Sheets

DETECTING METHOD AND APPARATUS USING A PROGRAMMABLE MEMORY DEVICE FOR STORING A DIGITIZED REFERENCE VALUE

BACKGROUND OF THE INVENTION

1. Field of the Invention

The invention relates to the field of detectors, more particularly to a detecting method and apparatus using a programmable memory device to store digitized reference values, thereby obviating the need for variable resistors to set the reference values in order to simplify the manufacture of the detecting apparatus.

2. Description of the Related Art

Indoor detecting apparatuses are commonly found in building and housing structures for safety purposes. Examples of conventional indoor detecting apparatuses include carbon monoxide detectors, fuel gas detectors such as liquefied petroleum or natural gas detectors, smoke detectors, and temperature detectors. Since a building usually has a wide variety of detecting apparatuses installed therein, whenever one of the detecting apparatuses generates an alarm signal, there is a need to inspect which one of the detecting apparatuses has detected the presence of an emergency condition before the area where the emergency condition exists can be determined. This problem arises in the prior art because the conventional detecting apparatuses are designed primarily to detect only one type of emergency condition. Aside from the resulting confusion in the event of an emergency condition, the expense that is incurred when expanding the types of emergency conditions to be detected can be astronomical.

A conventional detecting apparatus generally includes a processing unit, a sensor, a reference voltage generator, and an alarm device constituted by an alarm sound generator and a lamp indicator. FIG. 1 is a schematic circuit block diagram of a conventional carbon monoxide detector 1. As shown, a carbon monoxide sensor 11 and a reference voltage generator 12 are connected to a processing unit 10. The processing unit 10 is further connected to an alarm sound generator 13, such as a buzzer, and a lamp indicator 14, such as a light emitting diode. The reference voltage generator 12 is a variable voltage divider that includes a variable resistor VR. A variable tap of the variable resistor VR is connected to the processing unit 10 so that a reference voltage can be provided to the latter.

During the manufacture of the detector 1, there is a need to calibrate the same by adjusting the variable resistor VR so that the appropriate reference voltage can be supplied to the processing unit 10. Initially, the carbon monoxide sensor 11 is placed in a standard environment, such as a tank that contains a standard carbon monoxide concentration. Thereafter, the variable tap of the variable resistor VR is adjusted with the use of a tool, such as a screwdriver, until the processing unit 10 activates the alarm sound generator 13 and the lamp indicator 14 upon detection by the processing unit 10 that the reference voltage provided by the reference voltage generator 12 has reached the signal output of the carbon monoxide sensor 11.

In use, when the detector 1 is installed in a room of a building that is to be detected, the carbon monoxide sensor 11 generates a signal output that varies according to the carbon monoxide concentration inside the room. In the event that the signal output of the carbon monoxide sensor 11 exceeds the reference voltage from the reference voltage generator 12, indicative of an emergency condition in which the carbon monoxide concentration inside the room has exceeded the standard carbon monoxide concentration that was determined beforehand during the manufacturing stage of the detector 1, the processing unit 10 activates the alarm sound generator 13 and the lamp indicator 14 to alert the tenants of the building.

It is noted that adjustment of the variable resistor VR when calibrating the detector 1 is a time consuming task and is prone to human error.

SUMMARY OF THE INVENTION

Therefore, the main object of the present invention is to provide a detecting method and apparatus using a programmable memory device to store a digitized reference value, thereby obviating the need for a variable resistor to set the reference value when calibrating the detecting apparatus to simplify the manufacture of the detecting apparatus and to minimize the risk of human error.

Another object of the present invention is to provide a detecting method and apparatus which can include more than one type of sensor to expand the utility of the detecting apparatus without resulting in a large increase in equipment cost and equipment space.

According to one aspect of the invention, a detecting method comprises:

(a) placing a sensor in a standard environment such that the sensor generates a reference signal output corresponding to a detected condition in the standard environment;

(b) converting the reference signal output of the sensor into a digitized reference value;

(c) storing the digitized reference value in a programmable memory device;

(d) installing the sensor in an environment to be detected such that the sensor generates a detected signal output that varies according to the detected condition in the environment to be detected;

(e) converting the detected signal output of the sensor into a digitized detected value;

(f) comparing the digitized detected value with the digitized reference value stored in the programmable memory device; and (g) generating an alarm output when the digitized detected value exceeds the digitized reference value.

Preferably, steps (b), (c), (e) and (f) are jointly implemented using a single processing device.

According to another aspect of the invention, a detecting apparatus comprises a sensor for generating a signal output that varies according to a detected condition, a programmable memory device, an alarm device for generating an alarm output when activated, and a processing device connected to the sensor, the programmable memory device and the alarm device. The processing device includes a converting unit for converting the signal output of the sensor into a digitized value, a memory programming unit for storing a reference value in the programmable memory device, and a comparing unit for comparing the digitized value from the converting unit with the reference value in the programmable memory device. The processing device is operable selectively in a calibrating mode and a detecting mode. Operation of the processing device in the calibrating mode while the sensor is placed in a standard environment enables the memory programming unit to store the digitized value from the converting unit as the reference value in the programmable memory device. Operation of the processing device in the detecting mode while the sensor is installed in an environment to be detected enables the processing device to activate the alarm device upon detection by the comparing unit that the digitized value from the converting unit has exceeded the reference value in the programmable memory device.

According to a further aspect of the invention, a detecting apparatus comprises a first sensor for generating a first signal output that varies according to a first detected condition, a second sensor for generating a second signal output that varies according to a second detected condition, a programmable memory device, an alarm device for generating an alarm output when activated, and a processing device connected to the first and second sensors, the programmable memory device and the alarm device. The processing device includes a converting unit for converting the first and second signal outputs of the first and second sensors into first and second digitized values, respectively, a memory programming unit for storing first and second reference values in the programmable memory device, and a comparing unit for comparing the first and second digitized values from the converting unit with the first and second reference values in the programmable memory device, respectively. The processing device is operable selectively in a first calibrating mode, a second calibrating mode and a detecting mode. Operation of the processing device in the first calibrating mode while the first sensor is placed in a first standard environment enables the memory programming unit to store the first digitized value from the converting unit as the first reference value in the programmable memory device. Operation of the processing device in the second calibrating mode while the second sensor is placed in a second standard environment enables the memory programming unit to store the second digitized value from the converting unit as the second reference value in the programmable memory device. Operation of the processing device in the detecting mode while the first and second sensors are installed in an environment to be detected enables the processing device to activate the alarm device upon detection by the comparing unit that one of the first and second digitized values from the converting unit has exceeded the respective one of the first and second reference values in the programmable memory device.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
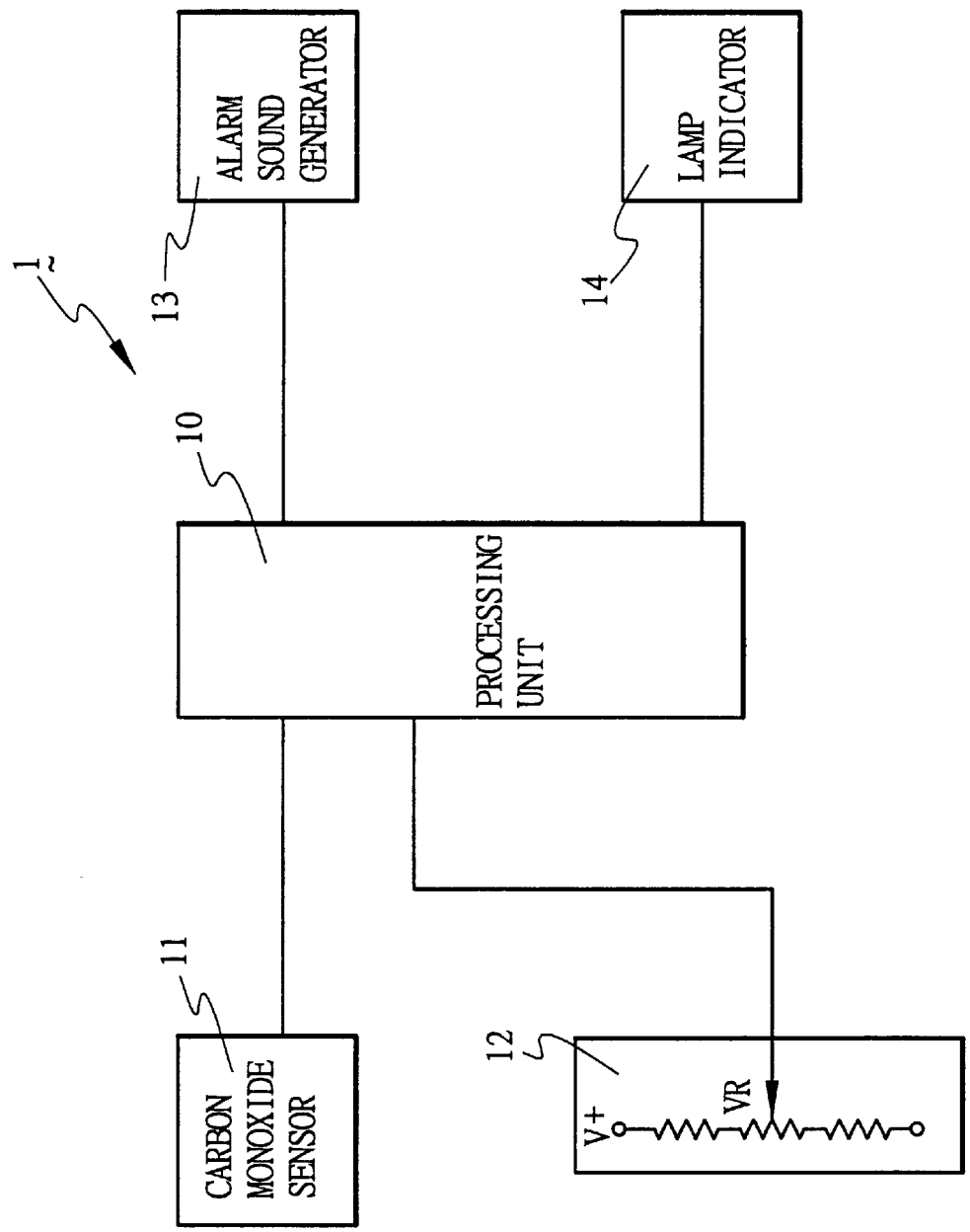
FIG. 1 is a schematic circuit block diagram of a conventional carbon monoxide detector.

Before the present invention is described in greater detail, it should be noted that like elements are denoted by the same reference numerals throughout the disclosure.

Figure 2:
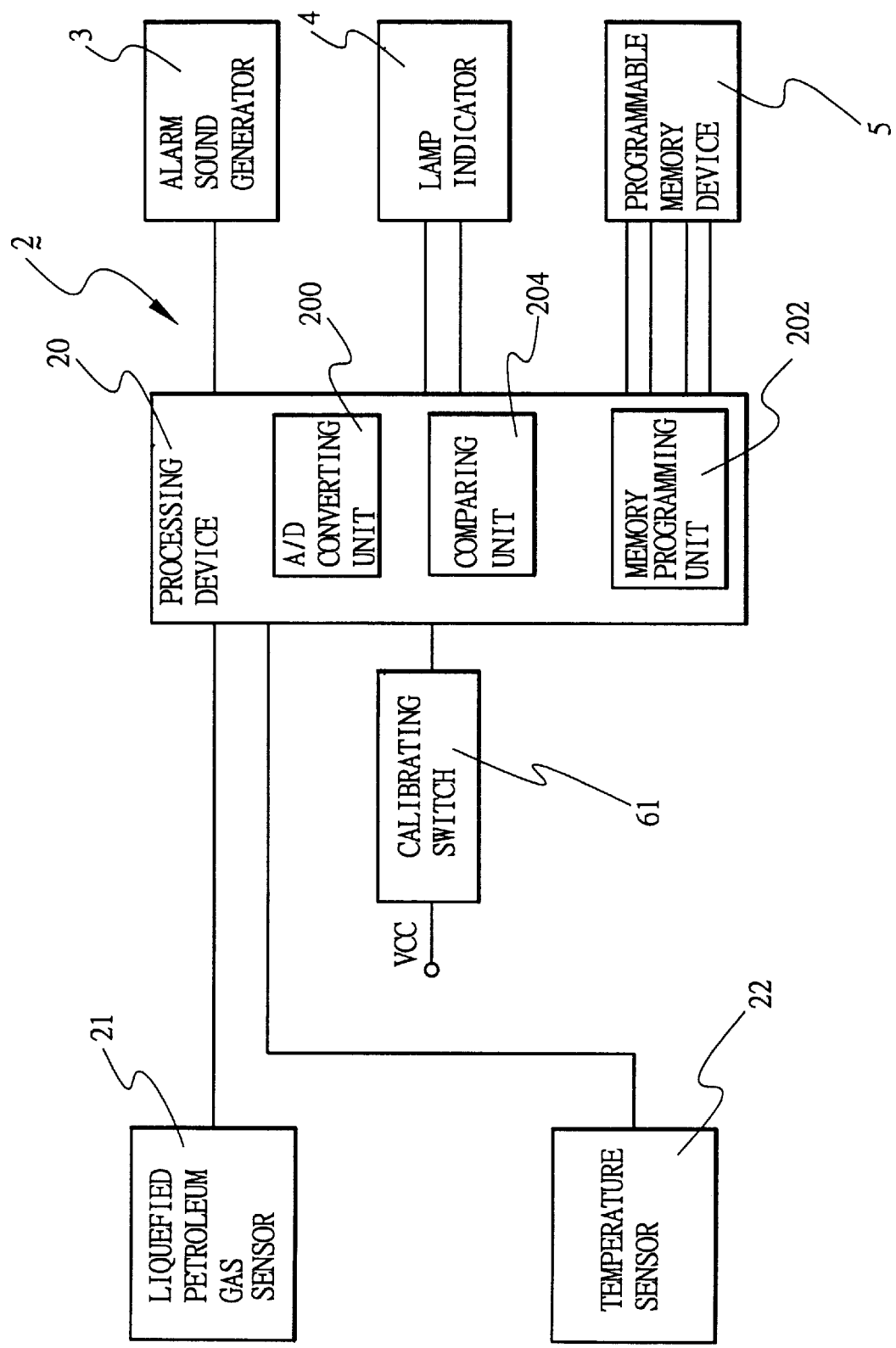
FIG. 2 is a schematic circuit block diagram of the first preferred embodiment of a detecting apparatus according to the present invention.

Referring to FIG. 2, the first preferred embodiment of a detecting apparatus 2 according to the present invention is shown to comprise a processing device 20 having sensor inputs connected respectively to a fuel gas sensor, such as a liquefied petroleum gas sensor 21, and a temperature sensor 22, and device outputs connected respectively to an alarm sound generator 3, such as a buzzer, and a lamp indicator 4, such as a light emitting diode. The alarm sound generator 3 and the lamp indicator 4 cooperatively form an alarm device. The detecting apparatus 2 further comprises a programmable memory device 5, such as an electrically erasable programmable read-only memory (EEPROM), having data lines and address lines connected to the processing device 20. The programmable memory device 5 is used to store a reference value corresponding to a standard fuel gas concentration therein. The processing device 20 includes an analog-to-digital (A/D) converting unit 200, a memory programming unit 202 and a comparing unit 204.

During the manufacture of the detecting apparatus 2, there is a need to calibrate the same in order to store the reference value in the programmable memory device 5. Initially, the liquefied petroleum gas sensor 21 is placed in a standard environment, such as a tank that contains a standard fuel gas concentration. The sensor 21 is a known device for generating a signal output that varies according to the fuel gas concentration that is detected thereby. Thereafter, a calibrating switch 61 connected to the processing device 20 is operated to initiate operation of the latter in a calibrating mode. At this time, the A/D converting unit 200 of the processing device 20 converts the signal output of the sensor 21 into a digitized reference gas concentration value, and the memory programming unit 202 stores the reference gas concentration value from the A/D converting unit 200 in a particular memory space of the programmable memory device 5. The temperature sensor 22 is a known device for generating a signal output that varies according to the temperature that is detected thereby. In the present embodiment, the processing device 20 has been programmed beforehand with a reference temperature value, such as 60° C.

In use, the liquefied petroleum gas sensor 21 and the temperature sensor 22 are installed inside a room that is to be detected. When the calibrating switch 61 is in a non-operated state, the processing device 20 is operated in a detecting mode. In the detecting mode, the processing device 20 retrieves the reference gas concentration value stored in the programmable memory device 5. The A/D converting unit 200 converts the signal outputs of the sensors 21, 22 into corresponding digitized sensor values, and the comparing unit 204 proceeds to compare the digitized sensor values with the reference gas concentration value and the reference temperature value, respectively. In the event that the sensor value of the temperature sensor 22 exceeds the reference temperature value, indicative of an emergency condition in which the temperature inside the room has exceeded the standard temperature of 60° C. that was set beforehand during the manufacturing stage of the detecting apparatus 2, the processing device 20 activates the alarm sound generator 3 and the lamp indicator 4 to generate a fire alarm output. In the event that the sensor value of the sensor 21 exceeds the reference gas concentration value, indicative of an emergency condition in which the fuel gas concentration inside the room has exceeded the standard fuel gas concentration that was set beforehand during the manufacturing stage of the detecting apparatus 2, the processing device 20 activates the alarm sound generator 3 and the lamp indicator 4 to generate a gas alarm output.

Figure 3:
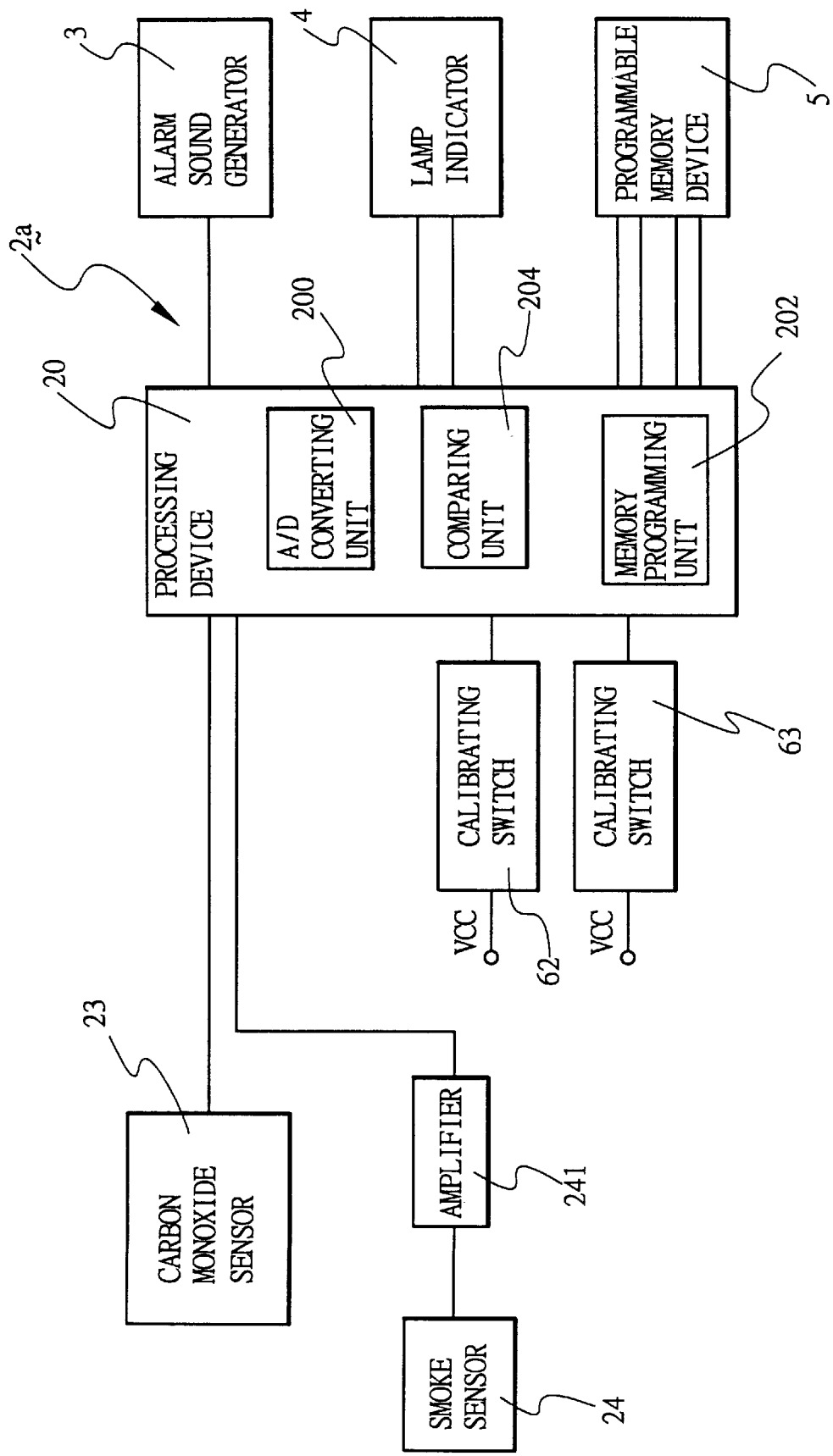
FIG. 3 is a schematic circuit block diagram of the second preferred embodiment of a detecting apparatus according to the present invention.

Referring to FIG. 3, the second preferred embodiment of a detecting apparatus 2a according to the present invention is shown to comprise a processing device 20 having sensor inputs connected respectively to a carbon monoxide sensor 23 and a smoke sensor 24, and device outputs connected respectively to an alarm sound generator 3, such as a buzzer, and a lamp indicator 4, such as a light emitting diode. The alarm sound generator 3 and the lamp indicator 4 cooperatively form an alarm device. The detecting apparatus 2a further comprises a programmable memory device 5, such as an electrically erasable programmable read-only memory (EEPROM), having data lines and address lines connected to the processing device 20. The programmable memory device 5 is used to store a first reference value corresponding to a standard carbon monoxide concentration, and a second reference value corresponding to a standard smoke density therein. As with the previous embodiment, the processing device 20 includes an analog-to-digital (A/D) converting unit 200, a memory programming unit 202 and a comparing unit 204.

During the manufacture of the detecting apparatus 2a, there is a need to calibrate the same in order to store the first and second reference values in the programmable memory device 5. To store the first reference value in the programmable memory device 5, the carbon monoxide sensor 23 is placed in a standard environment, such as a tank that contains a standard carbon monoxide concentration. The carbon monoxide sensor 23 is a known device for generating a signal output that varies according to the carbon monoxide concentration that is detected thereby. Thereafter, a calibrating switch 62 connected to the processing device 20 is operated to initiate operation of the latter in a first calibrating mode. At this time, the A/D converting unit 200 of the processing device 20 converts the signal output of the carbon monoxide sensor 23 into the digitized first reference value, and the memory programming unit 202 stores the first reference value from the A/D converting unit 200 in a first memory space of the programmable memory device 5.

To store the second reference value in the programmable memory device 5, the smoke sensor 24 is placed in another standard environment, such as a tank that contains a standard smoke density. The smoke sensor 24 is a known device for generating a signal output that varies according to the smoke density that is detected thereby. Thereafter, a calibrating switch 63 connected to the processing device 20 is operated to initiate operation of the latter in a second calibrating mode. At this time, the A/D converting unit 200 of the processing device 20 converts the signal output of the smoke sensor 24 into the digitized second reference value, and the memory programming unit 202 stores the second reference value from the A/D converting unit 200 in a second memory space of the programmable memory device 5.

In this embodiment, the smoke sensor 24 can be a photoelectric smoke sensor or an ionization smoke detector.

In case a photoelectric smoke sensor is in use, an infrared light emitting diode and an infrared light receiving diode of the smoke sensor are provided inside a chamber. The processing device 20 activates the infrared light emitting diode to emit light at fixed intervals, such as every 5 seconds. When smoke enters into the chamber, the smoke particles scatter and reflect light to the infrared light receiving diode, thereby enabling the latter to generate a current signal that corresponds to the density of the smoke inside the chamber. An amplifier 241 amplifies the current signal and provides the corresponding signal output to the processing device 20.

In case an ionization smoke detector is in use, a sensing chamber of the ionization smoke detector is supplied with a small amount of radioactive material to ionize the air in the sensing chamber, thereby rendering the air conductive and permitting electrical current to flow through the air between two charged electrodes. The sensing chamber thus has electrical conductance. When smoke enters into the sensing chamber, the smoke particles attach themselves to the ions in the air to decrease the electrical conductance of the air in the sensing chamber, thereby resulting in reduced mobility and in reduced electrical conductance of the sensing chamber in accordance with the density of the smoke inside the sensing chamber. The signal output of the ionization smoke detector corresponds to the electrical conductance of the sensing chamber and is detected by the processing device 20.

In use, the carbon monoxide sensor 23 and the smoke sensor 24 are installed inside a room that is to be detected. When neither one of the calibrating switches 62, 63 is in an operated state, the processing device 20 is operated in a detecting mode. In the detecting mode, the processing device 20 retrieves the first and second reference values stored in the programmable memory device 5. The A/D converting unit 200 converts the signal outputs of the sensor 23 and the amplifier 24 into corresponding digitized sensor values, and the comparing unit 204 proceeds to compare the digitized sensor values with the first and second reference values, respectively.

In the event that the sensor value of the carbon monoxide sensor 23 exceeds the first reference value, indicative of an emergency condition in which the carbon monoxide concentration inside the room has exceeded the standard carbon monoxide concentration that was set beforehand during the manufacturing stage of the detecting apparatus 2a, the processing device 20 activates the alarm sound generator 3 and the lamp indicator 4 to generate an alarm output after an appropriate time period based on the UL-2034 standard set for harmful exposure to carbon monoxide. Based on the UL-2034 standard, exposure to 100 ppm, 200 ppm and 400 ppm of carbon monoxide should not exceed 90 minutes, 35 minutes and 15 minutes, respectively, to avoid any harmful effect due to carbon monoxide. In the preferred embodiment, the alarm sound generator 3 and the lamp indicator 4 are activated 72 minutes after detection that the carbon monoxide concentration has exceeded 100 ppm, 23 minutes after detection that the carbon monoxide concentration has exceeded 200 ppm, and 8 minutes after detection that the carbon monoxide concentration has exceeded 400 ppm.

In the event that the sensor value of the smoke sensor 24 exceeds the second reference value, indicative of an emergency condition in which the smoke density inside the room has exceeded the standard smoke density that was set beforehand during the manufacturing stage of the detecting apparatus 2a, the processing device 20 activates the alarm sound generator 3 and the lamp indicator 4 to generate a smoke alarm output.

Figure 4:
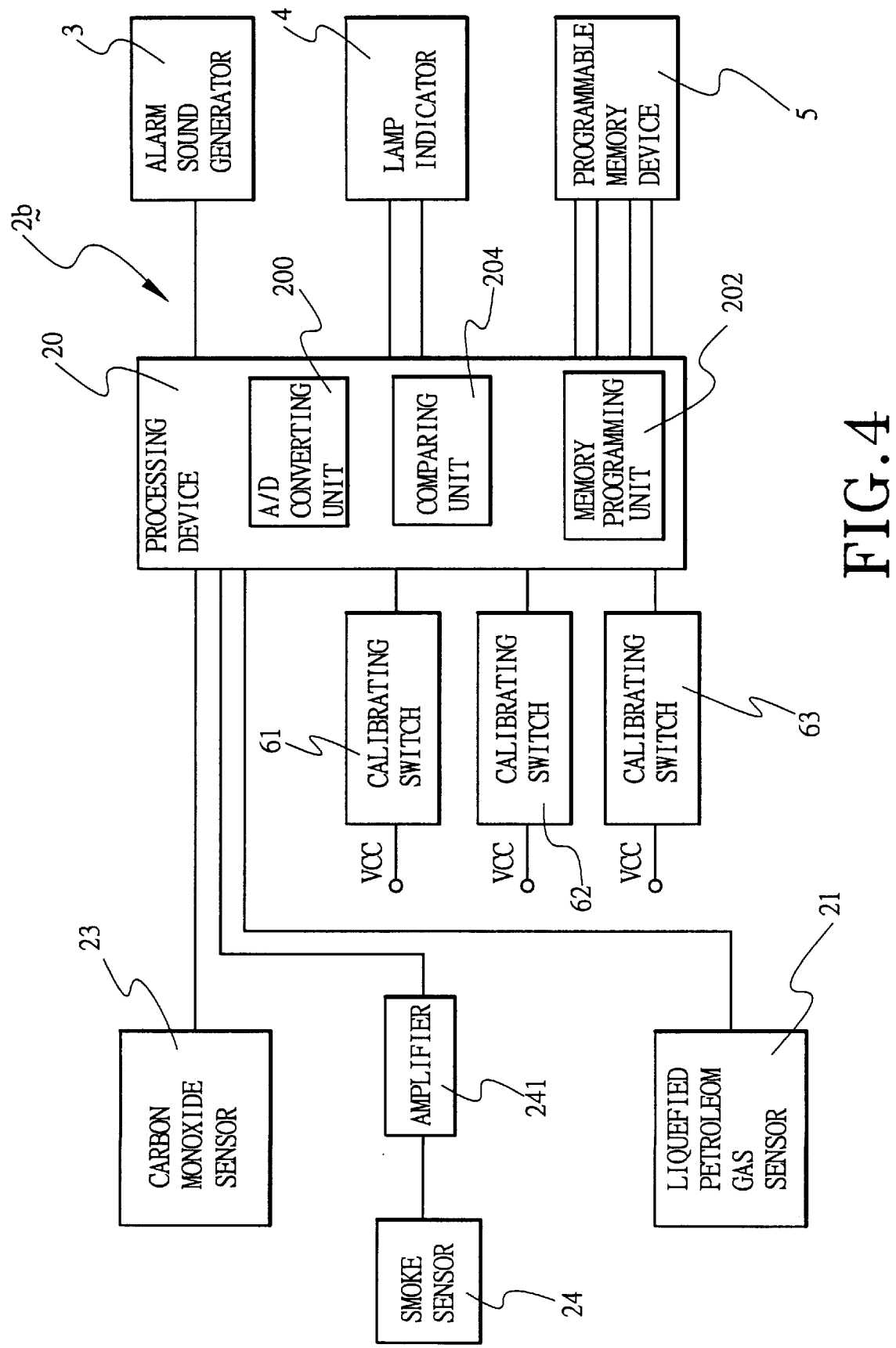
FIG. 4 is a schematic circuit block diagram of the third preferred embodiment of a detecting apparatus according to the present invention.

Referring to FIG. 4, the third preferred embodiment of a detecting apparatus 2b according to the present invention is shown to comprise a processing device 20 having sensor inputs connected respectively to a carbon monoxide sensor 23, a smoke sensor 24 and a fuel gas sensor, such as a liquefied petroleum gas sensor 21, and device outputs connected respectively to an alarm sound generator 3, such as a buzzer, and a lamp indicator 4, such as a light emitting diode. The alarm sound generator 3 and the lamp indicator 4 cooperatively form an alarm device. The detecting apparatus 2b further comprises a programmable memory device 5, such as an electrically erasable programmable read-only memory (EEPROM), having data lines and address lines connected to the processing device 20. The programmable memory device 5 is used to store a first reference value corresponding to a standard carbon monoxide concentration, a second reference value corresponding to a standard smoke density, and a third reference value corresponding to a standard fuel gas concentration therein. As with the previous embodiment, the processing device 20 includes an analog-to-digital (A/D) converting unit 200, a memory programming unit 202 and a comparing unit 204.

During the manufacture of the detecting apparatus 2b, there is a need to calibrate the same in order to store the first, second and third reference values in the programmable memory device 5. A calibrating switch 61 connected to the processing device 20 is operated to initiate operation of the latter in a first calibrating mode in which the first reference value is stored in a first memory space of the programmable memory device 5 in a manner similar to the calibration of the detecting apparatus 2 of the first preferred embodiment. Calibrating switches 62, 63 are similarly connected to the processing device 20 and are individually operable to initiate operation of the processing device 20 in a second or third calibration mode in which the second or third reference value is stored in a corresponding second or third memory space of the programmable memory device 5 in a manner similar to the calibration of the detecting apparatus 2a of the second preferred embodiment.

In use, the sensors 21, 23, 24 are installed inside a room that is to be detected. When none of the calibrating switches 61, 62, 63 is in an operated state, the processing device 20 is operated in a detecting mode. As with the previous embodiments, the processing device 20 activates the alarm sound generator 3 and the lamp indicator 4 to generate an alarm output in the event that the sensor value of any one of the sensors 21, 23, 24 exceeds the corresponding one of the first, second and third reference values.

Since the reference values are stored in a programmable memory device in the detecting apparatus of this invention, the need for variable resistors to set the reference values has been obviated to simplify calibration of the detecting apparatus and to minimize the risk of human error. In addition, the detecting apparatus can include more than one type of sensor to expand the utility of the detecting apparatus without resulting in a large increase in equipment cost and equipment space. Moreover, the detecting apparatus allows further expansion of the functions thereof by programming the processing device to include a built-in sensor testing function for detecting defective ones of the sensors. The processing device can be further programmed to adjust automatically the reference values in the programmable memory device to compensate for degradation of the corresponding sensor due to use of the latter over a period of time.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A detecting apparatus comprising:
    a first sensor for generating a first signal output that varies according to a first detected condition;
    a second sensor for generating a second signal output that varies according to a second detected condition;
    a programmable memory device;
    an alarm device for generating an alarm output when activated; and
    a processing device connected to said first and second sensors, said programmable memory device and said alarm device, said processing device including a converting unit for converting the first and second signal outputs of said first and second sensors into first and second digitized values, respectively, a memory programming unit for storing first and second reference values in said programmable memory device, and a comparing unit for comparing the first and second digitized values from said converting unit with the first and second reference values in said programmable memory device, respectively, said processing device being operable selectively in a first calibrating mode, a second calibrating mode and a detecting mode;
    operation of said processing device in the first calibrating mode while said first sensor is placed in a first standard environment enabling said memory programming unit to store the first digitized value from said converting unit as the first reference value in said programmable memory device;
    operation of said processing device in the second calibrating mode while said second sensor is placed in a second standard environment enabling said memory programming unit to store the second digitized value from said converting unit as the second reference value in said programmable memory device;
    operation of said processing device in the detecting mode while said first and second sensors are installed in an environment to be detected enabling said processing device to activate said alarm device upon detection by said comparing unit that one of the first and second digitized values from said converting unit has exceeded the respective one of the first and second reference values in said programmable memory device.

2. The detecting apparatus as claimed in claim 1, wherein one of said first and second sensors includes a fuel gas sensor, and the other one of said first and second sensors includes a carbon monoxide sensor.

3. The detecting apparatus as claimed in claim 1, wherein one of said first and second sensors includes a carbon monoxide sensor, and the other one of said first and second sensors includes a smoke sensor.

4. The detecting apparatus as claimed in claim 1, wherein one of said first and second sensors includes a smoke sensor, and the other one of said first and second sensors includes a fuel gas sensor.

5. The detecting apparatus as claimed in claim 1, further comprising a temperature sensor connected to said processing device to provide a temperature signal output that varies according to temperature that is detected thereby, said processing device having a reference temperature value stored therein, said converting unit further converting the temperature signal output of said temperature sensor into a digitized temperature value, said comparing unit further comparing the digitized temperature value from said converting unit with the reference temperature value when said processing device is operated in the detecting mode, said processing device activating said alarm device upon detection by said comparing unit that the digitized temperature value from said converting unit has exceeded the reference temperature value.

6. The detecting apparatus as claimed in claim 1, further comprising calibrating switch means, connected to said processing device, for selecting operation of said processing device in one of the first calibration mode, the second calibration mode and the detecting mode.

7. The detecting apparatus as claimed in claim 1, wherein said alarm device includes an alarm sound generator.

8. The detecting apparatus as claimed in claim 1, wherein said alarm device includes a lamp indicator.

* * * * *